United States Patent [19]
Gossioux

[11] Patent Number: 5,817,646
[45] Date of Patent: Oct. 6, 1998

[54] POLAR LIPID COMPOSITION OF PLANT ORIGIN

[75] Inventor: Pierre Gossioux, Issy-les-Moulineaux, France

[73] Assignee: Laboratoires Inocosm, Chatenay-Malabry Cedex, France

[21] Appl. No.: 717,626

[22] Filed: Sep. 23, 1996

Related U.S. Application Data

[63] Continuation of Ser. No. 244,019, Nov. 1, 1994, abandoned.

[30] Foreign Application Priority Data

Nov. 15, 1991 [FR] France .................... 91 14081

[51] Int. Cl.⁶ .......................... A61K 9/107; A61K 9/127; A61K 31/685
[52] U.S. Cl. .................... 514/78; 514/937; 514/938; 514/943; 424/195.1; 424/450
[58] Field of Search ............ 514/78, 937, 938, 514/943; 424/195.1, 401, 450

[56] References Cited

U.S. PATENT DOCUMENTS

| | | | |
|---|---|---|---|
| 4,252,793 | 2/1981 | Altman | 514/78 |
| 4,280,996 | 7/1981 | Okamoto et al. | 514/78 |
| 4,323,563 | 4/1982 | Takami et al. | 514/78 |
| 4,372,949 | 2/1983 | Kodama et al. | 514/78 |
| 4,684,633 | 8/1987 | Imagawa et al. | 514/78 |
| 5,010,067 | 4/1991 | Handley et al. | 514/75 |
| 5,134,130 | 7/1992 | Shaw et al. | 514/78 |

FOREIGN PATENT DOCUMENTS

| | | |
|---|---|---|
| 0 278 505 | 8/1988 | European Pat. Off. . |
| 0 319 638 | 6/1989 | European Pat. Off. . |
| 0 433 242 | 6/1991 | European Pat. Off. . |
| 33 39907 | 5/1985 | Germany . |
| 38 15473 | 11/1989 | Germany . |
| 57-122018 | 7/1982 | Japan . |
| 60-224628 | 11/1985 | Japan . |
| 2 213 723 | 8/1989 | United Kingdom . |
| WO 89/02733 | 4/1989 | WIPO . |
| WO 89/10753 | 11/1989 | WIPO . |
| WO 92/21321 | 12/1992 | WIPO . |

OTHER PUBLICATIONS

Brunke, R.A., Spezifische Eigenschaften von Sphingosomen, *Seifen–Öle–Fette–Wachse,* vol. 116, No. 2, Feb. 2, 1990.

Patent Abstracts of Japan, vol. 13, No. 49 (C–565) 3 Feb. 1989 & JP, A. 63 243 016 (Kanebo Ltd) 7 Oct. 1988.

*Primary Examiner*—Herbert J. Lilling
*Attorney, Agent, or Firm*—Seidel, Gonda, Lavorgna & Monaco, PC

[57] ABSTRACT

A polar lipid composition of plant origin is provided for conveying an active agent and/or making it penetrate into a target cell. The composition is characterized in that it is comprised of an injectable, intra-articular, topical or ingestible aqueous emulsion of a polar lipid mixture rich in phospholipids, in glycolipids and in ceramides, having a composition which is substantially similar to that of the polar lipid constituents of lipid cytomembranes of cells. The mixture is obtained from a plant compound such as cereal flour or an extract such as bran or lipids extracted from cereals by means of chlorinated solvents.

17 Claims, 5 Drawing Sheets

POLAR LIPID COMPOSITION OF PLANT ORIGIN

This is a continuation Ser. No. 08/244,019 filed on Nov. 1, 1994 and now abandoned.

FIELD OF THE INVENTION

Background of the Invention

The present invention relates to a method of producing a polar lipid composition of plant origin which makes it possible to carry an active agent or to cause the agent to enter into a target cell.

For ecological reasons, it is currently sought to protect animals as much as possible and to avoid as far as possible using them in laboratories. Encouraged by the various animal protection organizations, this current tendency is such that products of animal origin are increasingly poorly received.

Independent of these concerns of a philosophical nature, the development of products arising from the animal kingdom might be curbed in the future. In fact, in recent years viruses of the prion type have been seen in the animal kingdom, and in particular in ruminants. These viruses attack the brain and nervous tissues and are responsible for extremely serious neurological effects. The propagation of such viruses in humans cannot be ruled out. It is feared that their development can have horrendous consequences.

Taking into account this uncertainty, there currently exists a prejudice against products arising from the animal kingdom.

In particular, it should be noted that certain products extracted from nervous tissues of bovine origin have already been banned by the Pharmacie Centrale des Hôpitaux de Paris (Central Pharmacy of Parisian Hospitals).

This new restraint is a source of difficulty due to the fact that products of animal origin are already found in a partially or totally synthesized form, while the use of plant products requires additional manipulations which can prove to be lengthy and expensive.

Within this context, researchers in fields such as dermatology or pharmacology tend increasingly to use products arising from the plant kingdom or products of marine origin to replace animal products, despite the increased difficulties thus encountered.

This research has resulted in the development of a new process, described in PCT publication No. WO-A-92/21 321 published Dec. 10, 1992, which makes its possible to obtain from a plant compound, such as cereal flour, or an extract such as bran, or lipids extracted from cereals by chlorinated solvents, a lipid mixture which is rich in phospholipids, glycolipids and ceramides. In particular, the process can be used to obtain a base lipid mixture which has the following composition by weight:

| | |
|---|---|
| ceramides | 90% |
| lecithins | 5% |
| galactolipids | 5% |

It has already been proposed to prepare, from this base lipid mixture, compositions which can be used in fields such as cosmetology or dermatology.

In accordance with the present invention, it has now been discovered that this same base lipid mixture of exclusively plant origin can have many other important applications, in particular, in the field of pharmacology.

Biologists have known for many years that all cells from the animal kingdom are surrounded by plasma membranes which constitute selective permeability barriers. These cytomembranes, the structure of which is roughly constant, consist essentially of a continuous double layer of lipid molecules arranged in parallel with each other (i.e., "lipid bilayer") and joined by their hydrophobic groups in which various membrane proteins are embedded.

The various lipid constituents which form the lipid bilayer of the plasma membrane can be divided into non-polar and polar constituents. There is no general classification for these polar lipid constituents which is universally recognized by those skilled in the art, but it is generally recognized that the following polar lipids are common constituents of the lipid bilayer:

phospholipids, such as lecithin, glycolipids or galactolipids, ceramides, sphingolipids and glycosphingolipids.

Each type of cell has a membrane composition of lipid constituents, especially of polar lipid constituents, which is specific to it. Those skilled in the art have been able to establish composition ranges specific to each type of cell membrane.

The table below gives, by way of example, the approximate lipid compositions of various cell membranes.

| Lipids (% by weight) | Hepatic plasma membrane | Plasma membrane of the erythrocytes | Myelin | Mitochondria (internal and external membranes) | Endoplasmic reticulum | E. coli |
|---|---|---|---|---|---|---|
| Cholesterol | 17 | 23 | 22 | 3 | 6 | 0 |
| Phosphatidylethanolamine | 7 | 18 | 15 | 35 | 17 | 70 |
| Phosphatidyserine | 4 | 7 | 9 | 2 | 5 | traces |
| Phosphatidylcholine | 24 | 17 | 10 | 39 | 40 | 0 |
| Sphingomyelin | 19 | 18 | 8 | 0 | 5 | 0 |
| Glycolipids | 7 | 3 | 28 | traces | traces | 0 |
| Others | 22 | 13 | 8 | 21 | 27 | 30 |

Summary of the Invention

This invention comprises a method for producing a polar lipid mixture of plant origin that is essentially identical to the composition of the polar lipid constituents of a target cell membrane. To practice this invention, one first selects a target cell membrane that is to be duplicated and then identifies the composition of the polar lipid constituents of this cell membrane. Using a lipid mixture obtained from a plant compound as a base mixture, successive fractionations are performed on this base lipid mixture to prepare an aqueous emulsion that has a polar lipid composition essentially identical to that of the target cell membrane. This polar lipid mixture is capable of enhancing the penetration of an active agent into or through the target cell membrane.

Another embodiment of the invention comprises a method of producing a polar lipid mixture which is combined with an active agent.

DETAILED DESCRIPTION OF THE INVENTION

Figure 1:
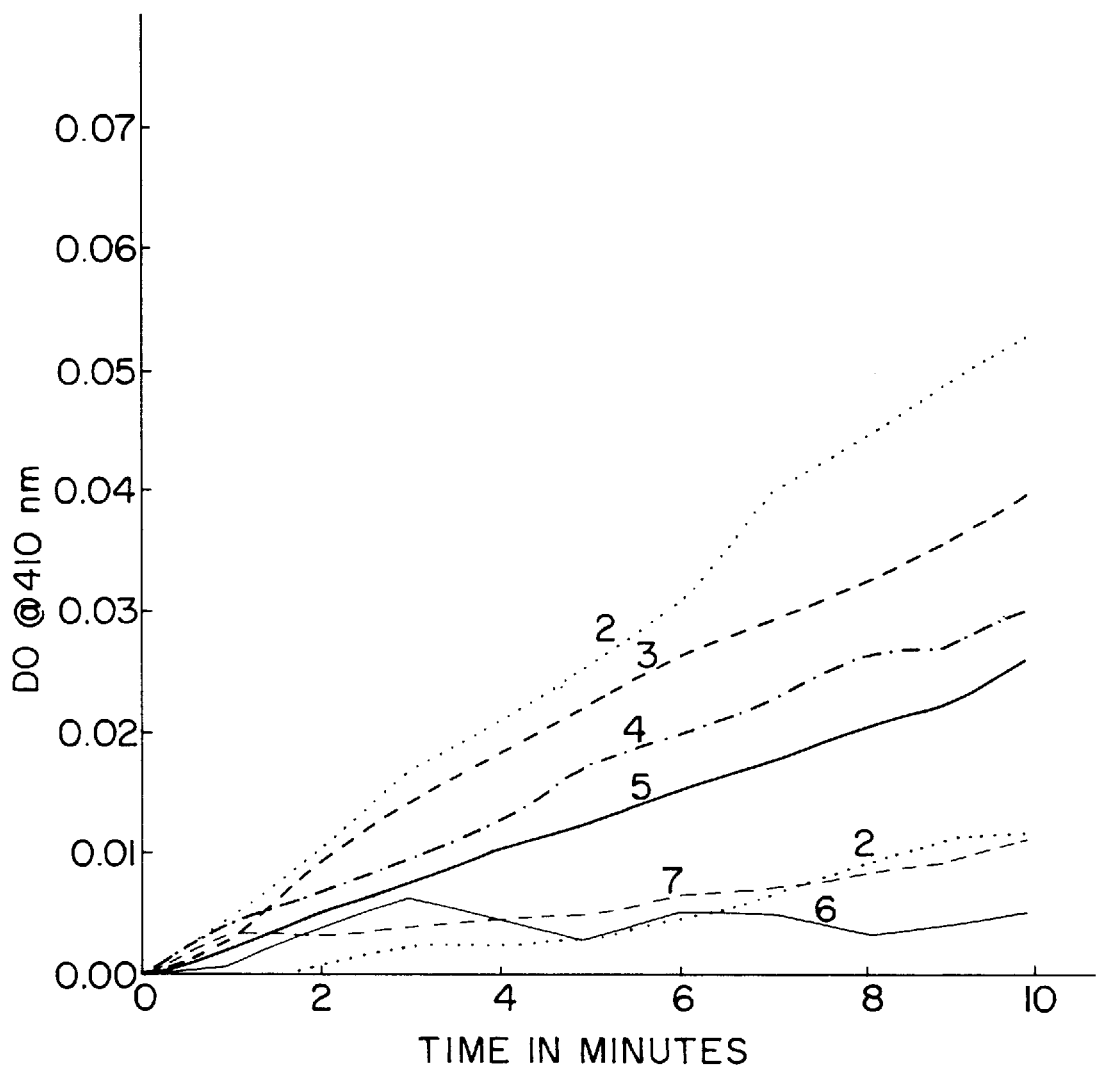
FIG. 1 represents the anti-elastase activity of the reference, oleic acid. Curve 1 corresponds to the sample prepared in accordance with the invention, curve 2 is the reference curve, and curve 3 corresponds to the kinetics in the absence of oleic acid. Curves 4 and 5 correspond to an oleic acid concentration of 0.1 $\mu$g/ml, while curves 6 and 7 correspond to an oleic acid concentration of 1.0 $\mu$g/ml.
Figure 2:
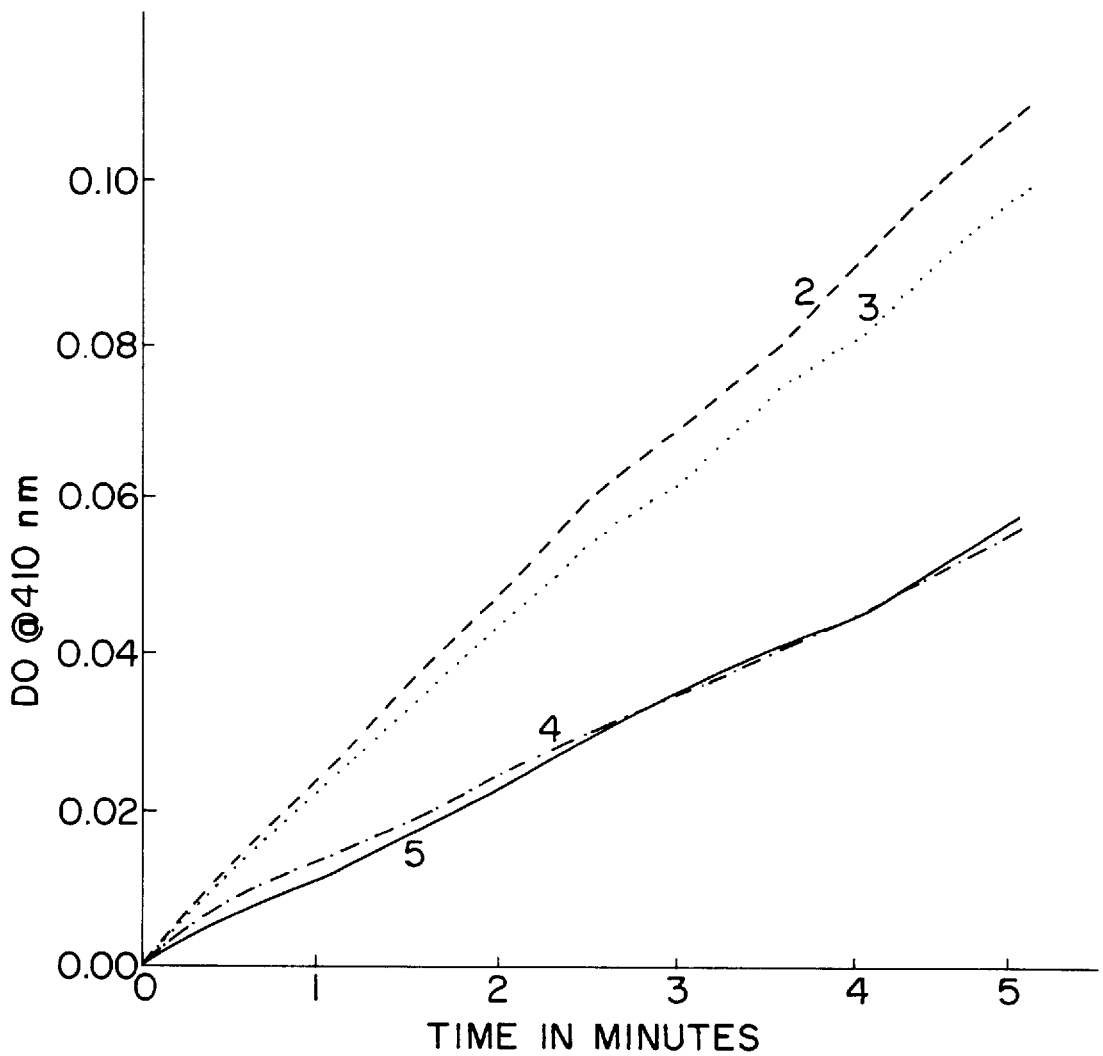
FIG. 2 represents the anti-elastase activity of Preparation A. Curves 1–5 correspond to the results for cell samples 1 to 5 shown in Table A.
Figure 3:
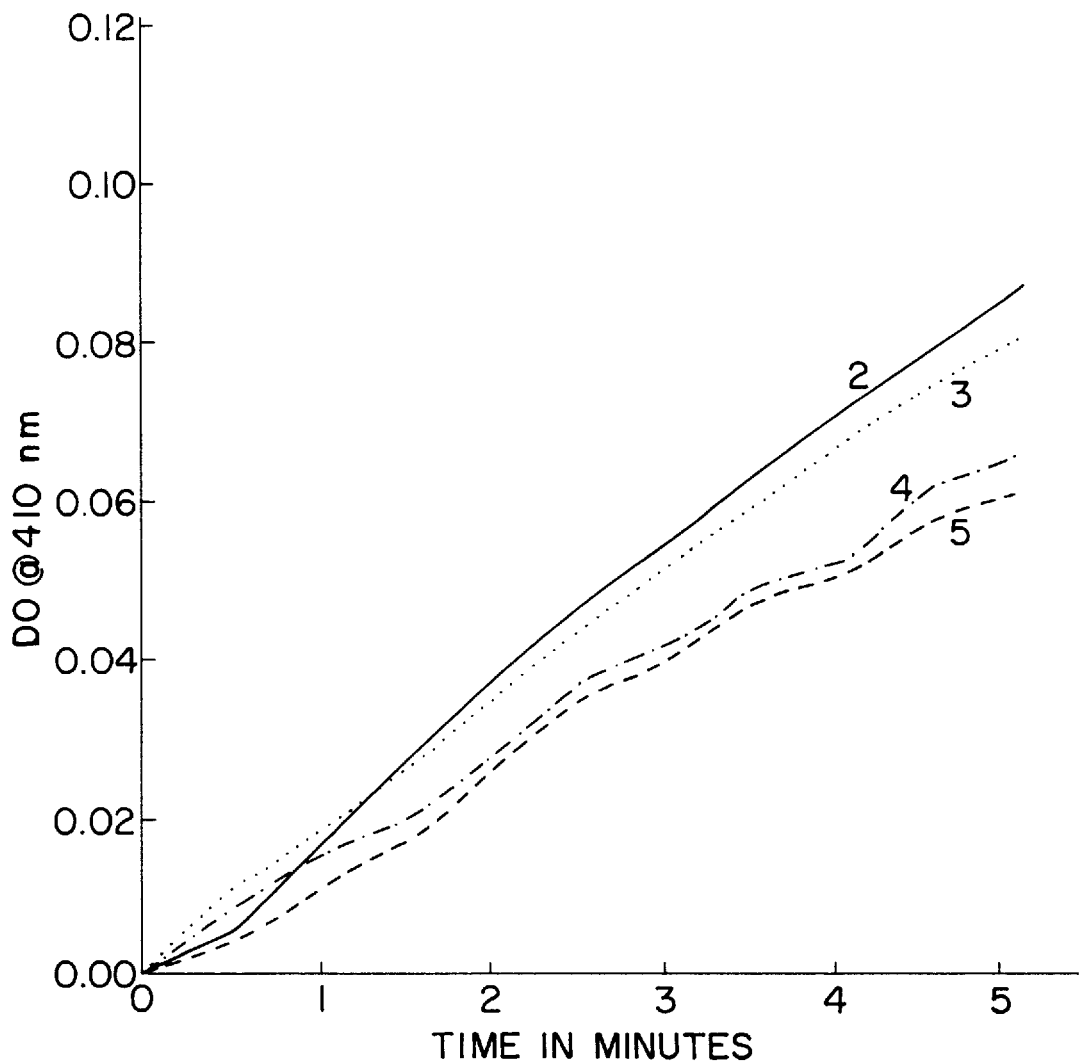
FIG. 3 represents the anti-elastase activity of Preparation B. Curves 1–5 correspond to the results for cell samples 1 to 5 shown in Table A.
Figure 4:
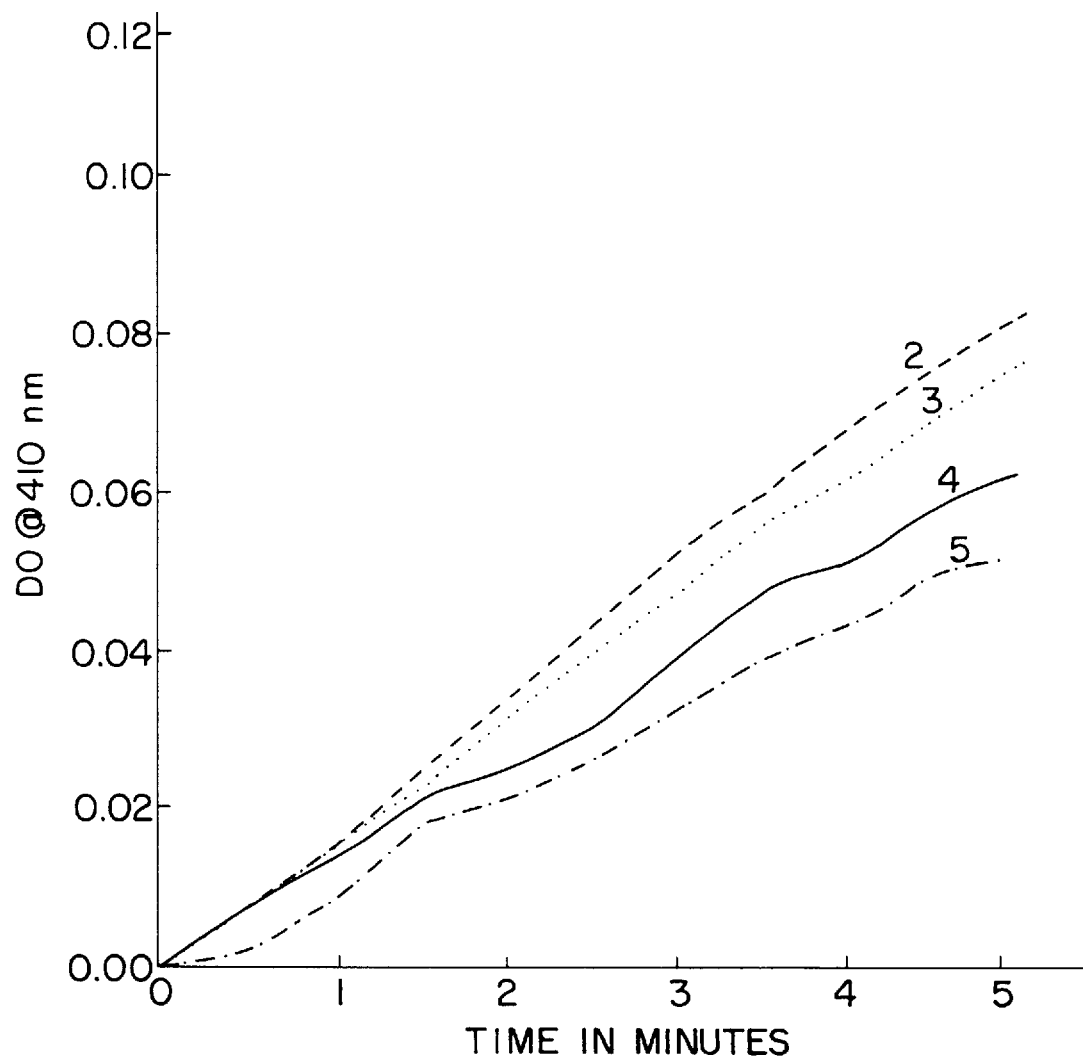
FIG. 4 represents the anti-elastase activity of Preparation C. Curves 1–5 correspond to the results for cell samples 1 to 5 shown in Table A.
Figure 5:
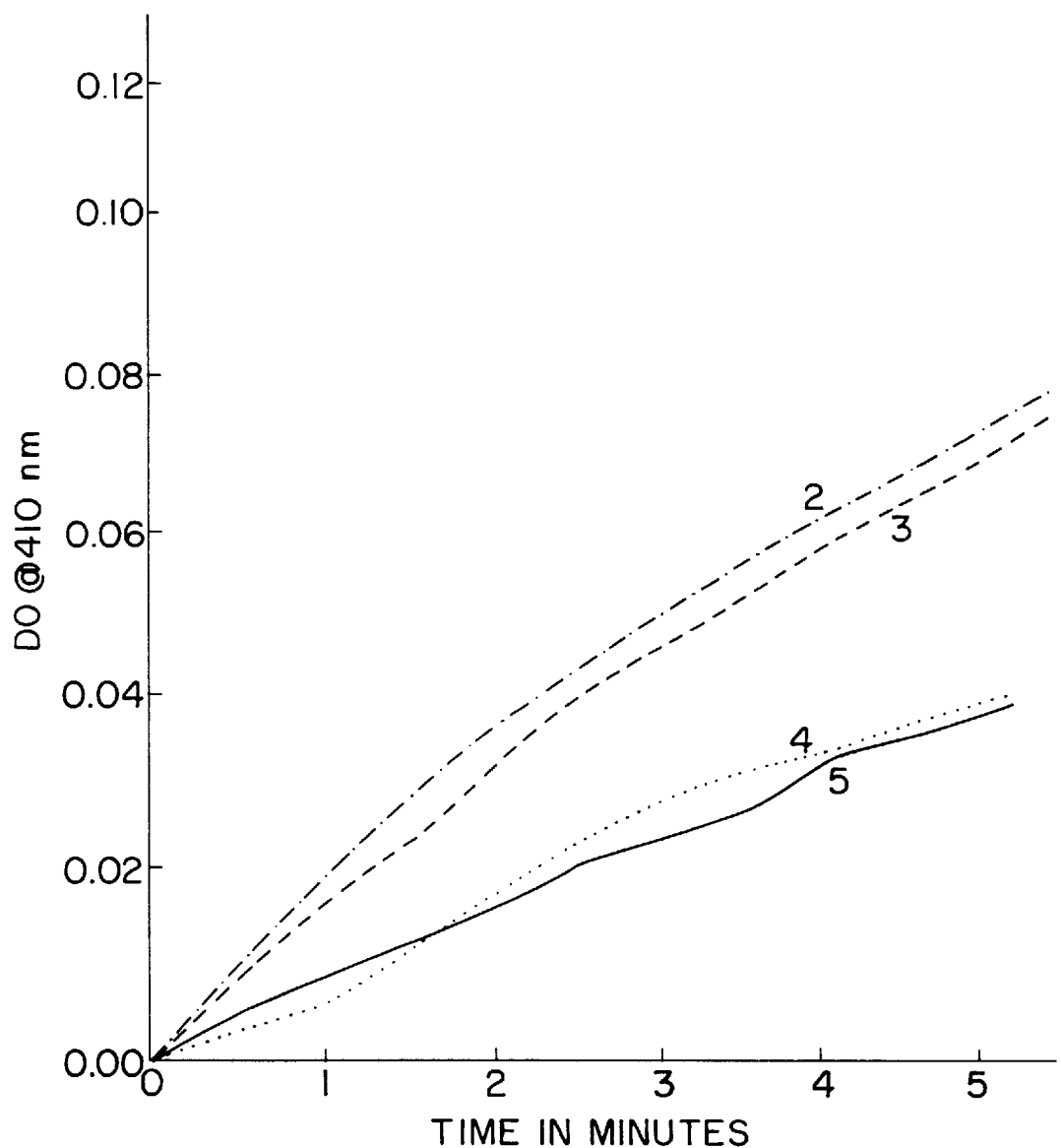
FIG. 5 represents the anti-elastase activity of Preparation D. Curves 1–5 correspond to the results for cell samples 1 to 5 shown in Table A.

Researchers have been able to prove that the polar constituents of lipid cytomembranes have a determining role on cell permeability and therefore influence the possibilities of penetration of active agents inside cells.

Now, in accordance with the invention, it has been realized that the above-mentioned base lipid mixture of plant origin has a composition roughly identical to that of the polar lipid constituents which are part of the composition of the lipid bi-layer of plasma membranes. From this base lipid mixture it is possible to produce, by successive fractionations, a "second" lipid mixture whose lipid composition is identical to that for a specific type of cell membrane (hereinafter "polar lipid mixture").

The idea on which the invention is based is to use this unique composition to produce, from the base polar lipid mixture, a composition in which the lipid composition of the lipid cytomembranes is duplicated, in order to carry an active agent into a target cell or to facilitate the entry of an active agent into a target cell.

To this end, one embodiment of the invention comprises a polar lipid mixture of plant origin, that can be injected, used intra-articularly, applied topically or ingested. This polar lipid mixture, which is an aqueous emulsion with a high concentration of phospholipids, and in particular in lecithin, and in ceramides, has a composition essentially identical to that of the polar lipid constituents of the lipid cytomembranes of the target cells. This polar lipid mixture is obtained from a plant compound, such as cereal flour, or an extract such as bran or lipids extracted from cereals.

This polar lipid mixture can be used for pharmaceuticals, cosmetics or, alternatively, as a dietary supplement and assume varied forms without departing from the scope of the invention. In certain cases, the polar lipid mixture can even constitute the active agent itself.

By way of example, it is known that an excess of cholesterol can cause deposits, on the internal wall of the arteries, of atheroma plaque consisting of a mixture of cells laden with fat and cholesterol crystals. While the reaction of the arterial wall with respect to the atheroma plaque is variable, it generally begins with a sclerosis (atherosclerosis) and is then followed by calcifications (Mönckeberg's arteriosclerosis). This in turn can be followed by thromboses (clotting of blood in the artery) and by aneurysms (dilation of the wall).

It has been possible to demonstrate that the polar lipid mixtures in accordance with the invention, and in particular ceramides and its derivatives, are emulsifying agents of cholesterol. The injection into the bloodstream of a patient whose arteries carry many atheroma plaques of a composition in accordance with the invention makes it possible to facilitate the removal of these deposits. In essence, the polar lipid mixture will extract the cholesterol from the arterial wall and then facilitate its discharge into the bloodstream.

More precisely, in order to obtain the composition needed to practice the invention, applicant used the notion of Hydrophile-Lipophile Balance or "HLB" which grades emulsifying agents according to their hydrophilicity or their lipophilicity. A low HLB (3 to 5) characterizes an emulsion with an oily continuous phase, while a higher HLB (10 to 12) characterizes an emulsion containing an aqueous continuous phase. HLB's higher than 12 are indicative of solubilization.

Using the notion of HLB, many methods, both theoretical and experimental, have been developed for determining the specific composition of a surface-active agent system needed to give the finest emulsion and, therefore, the optimum coupling of several surface-active agents.

According to the invention, in order to determine the optimum in vitro composition needed for the emulsification of cholesterol from the arterial wall, use was made of an experiment which measured the conductivity, for the amount of water needed to cause the phase inversion of an emulsion.

It was found that an HLB of 8 to 10 was optimal.

In accordance with a more preferred embodiment of the invention, the emulsion of the polar lipid mixture has a composition essentially identical to that of the lipid cytomembranes of a target cell and contains an active agent coated in a sheath of the polar lipid mixture.

Such a composition can, in another embodiment of the invention, contain a hydrating agent in combination, if appropriate, with additives such as vitamins A or E and coated in a sheath having a composition identical to that of the lipid cytomembranes of the cells of the epidermis and in particular of the stratum corneum. The hydrating agents utilized in these compositions can be liposoluble hygroscopic agents or humectants such as, for example, lanolin, polyunsaturated fatty acids, especially vitamin F, linoleic acid, $\gamma$-linolenic acid or eicosapentaenoic acid or alternatively, water-soluble agents such as glycerol, mucopolysaccharides, allantoin derivatives, amino acids, urea, sodium or potassium.

In such compositions, which can be used in controlling aging or treating burns, it is believed that the polar lipid mixture acts at two levels: it improves membrane permeability with respect to the active agent and, at the same time, the mixture itself contributes to the hydration of the cells. In fact, it has recently been possible to demonstrate the role, in mechanisms for hydration of the skin, of phospholipids and especially of ceramides which are capable of contributing to a better retention of water, of restructuring the epidermis and especially the intercomeocytic cement, and of improving the resistance of the skin to external assaults.

According to another embodiment, the invention can also assume the form of a medicinal composition intended for various therapeutic classes. Its active agent can assume varied forms and can preferably be chosen from the group formed by antibiotic agents, anti-inflammatory agents, corticoids, antiviral agents, anti-cancer agents and medicaments for cardiovascular pathologies.

Mention may more precisely be made, by way of example, of the possibility of carrying the following active agents:

| Therapeutic class | Active agents |
| --- | --- |
| Cardioangiology | Rutin |
| Endocrinology and hormones | Testosterone |
| Metabolism | Oils rich in γ-linolenic acid, eicosapentaenoic acid, docosahexaenoic acid |
| Rheumatology | Hydrocortisone NSAI (non-steroidal anti-inflammatories) |
| Immunoallergology | Allergens |

By using a polar lipid mixture with a composition corresponding to that of the lipid cytomembranes of the target cells which one desires to treat, it is possible to inject the active agent directly into the required site where it will selectively "attack" the target cell membrane. This selective attack of the target cell membrane makes it possible to use a reduced concentration and thus, as far as possible, to avoid side effects, while improving efficacy and yields.

The above-mentioned examples are not, of course, limiting and it is possible to envisage many other applications of the invention, consisting especially in making an element such as sodium re-enter a deficient cell.

In all cases, the polar lipid sheath constitutes, by virtue of its selective composition, a vector which makes it possible to improve the permeability of the target cell for the active product.

It is also possible, according to another embodiment of the invention, to incorporate in the composition, as active agent, which is not strictly speaking a "treating" compound but one which is a toxic substance selective for a pathogenic agent, especially a virus, a bacterium or a fungus.

In this instance, the polar lipid sheath acts as a "snare" for trapping the pathogenic agent and facilitating its removal.

According to this embodiment of the invention, it is possible to use this aspect of the invention for controlling AIDS. By coating 3'-azido-3'deoxythymidine, AZT, in a polar lipid sheath whose composition corresponds to that of the lipid cytomembranes of leukocytes, the AIDS virus can, in effect, recognize the constituent lipids of the sheath which correspond to its normal route of entry into the cells and thus come into contact with AZT so as to promote its destruction.

The polar lipid mixture of the present invention can also be used as a vehicle for the delivery of a vaccine component necessary for reinforcing humoral and cell immunity.

The characteristics of the polar lipid mixture which forms the subject of the invention will be explained in detail in the examples below:

Example 1

A cosmetic composition was manufactured which has the following formula by weight:

| | |
| --- | --- |
| Vitamin E acetate | 0.5% |
| Hydrogenated lecithin | 0.5% |
| Ceramides | 0.5% |
| Vitamin A (1,000,000 IU/g) | 0.1% |
| Preserving agents + Water | |

This composition has proved to be very stable and has a specific feel which is pleasant to the users.

Example 2

A test to ascertain the activity of a polar lipid mixture in accordance with the invention to protection by corticoids against a free radical attack was carried out in the laboratories of the Faculty of Pharmacy of Chatenay Malabry (France).

Red blood cells, isolated from their plasma, were subjected to an oxidative-type attack under controlled and standardized conditions, which enabled them to utilize all their enzymatic and molecular equipment in order to resist this attack, until modification of the cell membrane and bursting and lysis of the cell have occurred.

More precisely, various preparations containing red blood cells were subjected to an attack by organic free radicals produced by thermal decomposition of a specific water-soluble nitrogenous compound: 2,2-azobis-2-amidinopropane hydrochloride (100 mM), under an atmosphere of air at 37° C. It was thus possible to produce a known and constant amount of peroxydized radicals.

At regular time intervals, a small volume of supernatant was withdrawn from the preparation and its haemoglobin content was analyzed by spectrophotometry (1=540 nm or 405 nm).

The resistance of the population of red blood cells of each of the preparations tested was then expressed by the half-lysis time, that is, the time for release of 50% of the haemoglobin content.

In order to carry out this test, isolated human red blood cells were washed and resuspended in a hematocrit (at 11%). These cells have the advantage of having a relatively short half-life (approximately 110 days) and of possessing all the molecular and enzymatic equipment for protection against free radicals, which enables them to be representative of the other cells of the body.

The following compositions in accordance with the invention were prepared for use in this experiment;

| Composition A | |
| --- | --- |
| Vitamin E acetate | 2% |
| Hydrogenated lecithin | 1% |
| Ceramides | 1% |
| Vitamin A acid | 0.05% |
| Preserving agents + Water | |
| Composition B | |
| Vitamin E acetate | 2% |
| Hydrogenated lecithin | 1% |
| Ceramides | 1% |
| Dexamethasone | 0.02% |
| Preserving agents + Water | |

The following test preparations were then produced:
1: Red blood cells
2: Red blood cells+Composition A (1/10)
3: Red blood cells+Composition B (1/10)

4: Red blood cells+Betneval (registered brand name) (1/10)

5: Red blood cells+Effederm (registered brand name) (1/10).

Betneval and Effederm correspond to commercial medicaments containing dexamethasone and Vitamin A acid, respectively, at concentrations similar to those of Compositions A and B shown above.

The table below gives the half-lysis times, T50, expressed in minutes, obtained for each of the preparations tested:

| Preparation | T50 |
| --- | --- |
| 1 (control) | 168 |
| 2 | 240 |
| 3 | 258 |
| 4 | 180 |
| 5 | 186 |

These results show that the addition of the two commercial products only very weakly protects the lifetime of the red blood cells subjected to a free radical "stress", whereas the two compositions in accordance with the invention which were tested made it possible to obtain a much better protection.

Example 3

A test to ascertain the activity of a polar lipid mixture in accordance with the invention on the inhibition of a specific enzyme, human leukocytic elastase (HLE), was carried out at the Connective Tissue Laboratory of the CNRS at Cretail (France). HLE is able to destroy elastin and therefore cause cell aging. HLE also detrimentally effects the arterial walls.

The activity of the mixture in accordance with the invention was compared with that of oleic acid, the reference substance.

This test measures the inhibition of the enzymatic activity by different preparations tested by following the kinetics at 410 nm of the degradation of a substrate, S, corresponding essentially to elastin: Me-O-Suc-Ala$_2$-Pro-Val-pNa(N-Methoxy-succinyl-Ala-Ala-Pro-Val-p-Nitroanilide). In this test, changes in the concentration of p-Nitroaniline, released due to the effect of the activity of HLE on the substrate, S, is measured over time.

In order to carry out these tests:

either 0.1M Tris-Cl+0.01% Triton X-100 at pH 8 or 0.1M Tris-HCl at pH 8 was used as the reaction buffer, B.

Generally, it was possible to observe a better inhibition in the Tris-HCl, but a lower enzymatic activity, than in the Tris-HCl+0.01% Triton X-100 buffer.

The composition of each mixture tested is summarized in Table A below:

TABLE A

| Cell No | 1 | 2 | 3 | 4 | 5 | Observations |
| --- | --- | --- | --- | --- | --- | --- |
| B (µl) | 1955 | 1965 | 1965 | 1945 | 1945 | |
| HLE (µl) | — | 10 | 10 | 10 | 10 | From a mother solution containing 100 µl/ml |
| Tested preparation (µl) diluted to 1/10th | 20 | — | — | 20 | 20 | |
| Substrate | 25 | 25 | 25 | 25 | 25 | From a solution containing 2.3 mg/ml |

Each of the cell samples were agitated for 30 minutes at 37° C. so as to allow the enzyme time to act on its substrate.

Spectrophotometer readings were taken at 410 nm relative to the p-Nitroaniline concentration and the results obtained were then transferred to Curves 1 to 5, which correspond to the cell samples of the same numbering. The Curve numbered 1 corresponds to the reference, whereas Curves 2 and 3 represent the kinetics in the absence of the tested preparations and Curves 4 and 5 represent the kinetics in the presence of these preparations.

On each of these curves, the time in min was recorded on the abscissa and the optical deviation, OD, read at 410 nm, was recorded on the ordinate.

The preparations tested were the following:

Preparation A: 1% Ceramide+1% hydrogenated lecithin

Preparation B: 1% Ceramide+1% hydrogenated lecithin +2% Vitamin E acetate

Preparation C: 1% Ceramide+1% hydrogenated lecithin +2% Vitamin E acetate+0.05% Vitamin A acid Preparation D: 1% Ceramide+1% hydrogenated lecithin +2% Vitamin E acetate+0.02% Dexamethasone.

For the reference oleic acid (FIG. 1), the procedure was altered in that seven measuring cells were used, from which, on each occasion, the curves corresponding to the monitoring of the kinetics of the release of p-Nitroaniline were established. Curves 1 to 3 correspond to the sample prepared in accordance with the invention, to the reference curve, and to the kinetics in the absence of oleic acid, respectively. Curves 4 and 5 correspond to an oleic acid concentration equal to 0.1 µg/ml, whereas curves 6 and 7 correspond to an oleic acid concentration of 1 µg/ml.

The curves corresponding to the reference, oleic acid, (FIG. 1) and to Preparations A to D (FIG. 2–5) are appended.

The percentage of inhibition of the anti-elastase activity of each of the different preparations after 10 min was measured on each of the curves and the following results were found:

| Reference oleic acid at 0.1 µg/ml | 36% |
| --- | --- |
| Reference oleic acid at 1.0 µg/ml | 84% |
| Preparation A | 45% |
| Preparation B | 24% |
| Preparation C | 29% |
| Preparation D | 51% |

These results demonstrate the anti-elastase activity of the inventive compositions and, in particular, of the use of ceramides.

This activity had until now never been demonstrated.

I claim:

1. A method for producing a polar lipid mixture of plant origin essentially identical to the composition of the polar lipid constituents of a target cell membrane, which method comprises:

(a) selecting a target cell membrane;

(b) identifying the lipid composition of the polar lipid constituents of the target cell membrane;

(c) obtaining a sufficient quantity of a base lipid mixture comprising phospholipids, glycolipids, and ceramides from plants having the essentially the following composition by weight:

| | |
|---|---|
| ceramides | 90% |
| lecithins | 05% |
| galactolipids | 05% |

(d) performing successive fractionations of the base lipid mixture to obtain an aqueous emulsion of phospholipids and ceramides having a polar lipid composition essentially identical to the target cell membrane.

2. A method according to claim 1 wherein the polar lipid mixture is obtained from a source selected from the group consisting of cereal flour, bran extract, and cereal extract.

3. A method according to claim 1, comprising the further step of combining the polar lipid mixture with an active agent.

4. A method according to claim 11 wherein the polar lipid mixture has a hydrophilic-lipophilic balance of between 8 and 10 to facilitate the removal of atheroma plaques.

5. A method according to claim 3 wherein the active agent is coated with the polar OZ lipid mixture.

6. A method according to claim 5 wherein the active agent is a hydrating agent.

7. A method according to claim 6 wherein the active agent comprises a hydrating agent and a vitamin selected from the group of vitamins A and E.

8. A method according to claim 5 wherein the active agent is selected from the group consisting of antibiotics, antiinflammatory agents, corticoids, antiviral agents, anticancer agents, and cardiovascular therapeutics.

9. A method according to claim 5 wherein the active agent is a toxic substance which is selectively toxic against a pathogenic agent.

10. A method according to claim 9 wherein the pathogenic agent is selected from the group consisting of a virus, a bacterium, or a fungus.

11. A method according to claim 9 wherein the active agent is 3'-azido-3'-deoxythymidine.

12. A method according to claim 3 wherein the active agent is an allergen carried to the target cell to stimulate an immune defense.

13. A method according to claim 3 wherein the active agent is a vaccine.

14. A method according to claim 5 wherein the active agent is an allergen carried to the target cell to stimulate an immune defense.

15. A method according to claim 5 wherein the active agent is a vaccine.

16. A method of treating a human patient with a polar lipid mixture of plant origin essentially identical to the composition of the polar lipid constituents of a target cell membrane, which method comprises:

(a) selecting a target cell membrane;

(b) identifying the lipid composition of the polar lipid constituents of the target cell membrane;

(c) obtaining a sufficient quantity of a base lipid mixture comprising phospholipids, glycolipids, and ceramides from plants having the essentially the following composition by weight:

| | |
|---|---|
| ceramides | 90% |
| lecithins | 05% |
| galactolipids | 05% |

(d) performing successive fractionations of the base lipid mixture to obtain an aqueous emulsion of phospholipids and ceramides having a polar lipid composition essentially identical to the target cell membrane; and (e) administering the product of step (d) to a patient.

17. A method according to claim 16 wherein the aqueous emulsion is combined with an active agent before administration to the patient and wherein the emulsion is capable of enhancing the penetration of the active agent into or through the target cell membrane.

* * * * *